United States Patent [19]

Hohler et al.

[11] Patent Number: 5,536,816
[45] Date of Patent: Jul. 16, 1996

[54] PROCESS FOR PRODUCING AMIDES USING CATALYTIC AMOUNTS OF AN N-HYDROXY COMPOUND

[75] Inventors: Markus Hohler, Möhlin; Peter Vogt, Aesch, both of Switzerland

[73] Assignee: Hoffmann-La Roche Inc., Nutley, N.J.

[21] Appl. No.: 196,750

[22] Filed: Feb. 15, 1994

[30] Foreign Application Priority Data

Feb. 19, 1993 [CH] Switzerland .............................. 518/93

[51] Int. Cl.⁶ ............................................... A61K 38/05
[52] U.S. Cl. ........................... 530/338; 530/333; 530/341
[58] Field of Search ..................................... 530/333, 345, 530/341, 342

[56] References Cited

U.S. PATENT DOCUMENTS 3,872,074   3/1975   Konig .................................... 260/112.5

OTHER PUBLICATIONS

Bodanszky, Principles of Peptide Synthesis, Springer–Verlag Chapter 1.1 pp.170–185–(1993).

Konig, et al. Eine neue Methode zur Synthese von peptiden: Aktivierung der Carboxyl mit Dicyclohexylcarbodiimid unter Zusatz von 1–Hydroxy–benzotriazolen, Chem. Ber 103, pp. 788–798 (1970).

Przybylski, et al Influence Of Additives On Supression Of Racemization In Peptide Synthesis Part I, Isonitroso Compounds And N–Arylsulfonyhydroxylamines As Additives Suppressing Racemization Of Amino Acides Rests In Peptide Synthesis by The DCCI Method, Roczniki Chemii, Ann. Soc. Chim. Polonorum Bd. 51, Nr. 5 pp. 939–949 (1977).

*Primary Examiner*—Christina Y. Chan
*Assistant Examiner*—David Lukton
*Attorney, Agent, or Firm*—George M. Gould; William H. Epstein; Bruce A. Pokras

[57] ABSTRACT

A process for the manufacture of amides, including peptides, by reacting a carboxylic acid with a primary or secondary amine in the presence of a carbodiimide and a catalytic amount of a N-hydroxy compound.

4 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 10 amino acids
      ( B ) TYPE: amino acid
      ( D ) TOPOLOGY: unknown ( i i ) MOLECULE TYPE: protein ( i i i ) HYPOTHETICAL: NO ( i v ) ANTI-SENSE: NO ( x i ) SEQUENCE DESCRIPTION: SEQ ID NO:1:

Val  Gln  Ala  Ala  Ile  Asp  Tyr  Ile  Asn  Gly
      1                   5                        10

PROCESS FOR PRODUCING AMIDES USING CATALYTIC AMOUNTS OF AN N-HYDROXY COMPOUND

BACKGROUND OF THE INVENTION

It is known that amides, including peptides, may be produced by reacting a carboxylic acid with a primary or secondary amine in the presence of dicyclohexylcarbodiimide (DCC) and a N-hydroxy compound. Zeitschrift für Naturforschung (B), 426 (1966) discloses that peptide formation from N-acylpeptides, which contain an optically active amino acid having a carboxyl terminal, proceeds practically free from racemization when the peptide formation is carried out using DCC with the addition of 2 tool equivalents of N-hydroxysuccinimide in tetrahydrofuran or dimethylformamide at −20° C. From Chemische Berichte 103 (1970), pages 788–798, 2024–2033, 2034–2040, it is known that the effect described above can also be observed when 1–2 mol equivalents of various 1-hydroxy-benzotriazoles, 1-hydroxy-2-oxoindolines, 3-hydroxy-4-oxo-3,4-dihydroquinazolines and 3-hydroxy-4-oxo-3,4-dihydro-1,2,3-benzotriazines are used in place of said 2 mol equivalents of N-hydroxysuccinimide. It is also known that certain N-hydroxy compounds may suppress the formation of byproducts in DCC activation. According to the Journal of Organic Chemistry 37, 288 (1972), 1 mol equivalent of N-hydroxysuccinimide was successful in suppressing the formation of N-acylureas (byproducts in DCC activation) in the reaction of one mol equivalent of 1-(9-adenyl)-2,3-O-isopropylidene-β-D-ribofuranuronic acid with benzyl esters of various amino acids and peptides. Chemische Berichte 106, 3626 (1973) discloses that the aminolysis of phenyl esters of amino acids and peptides substituted with electron-withdrawing groups is accelerated greatly by those N-hydroxy compounds, which have about the acidity of acetic acid, in polar solvents, especially with the use of 1 mol equivalent of 1-hydroxybenzotriazole, 1-hydroxy-2(1H)-pyridone and 3-hydroxy-4-oxo-3,4-dihydroquinazoline. According to Journal of the American Chemical Society 94, 3590 (1972), 1.1 mol equivalent of N-hydroxysuccinimide is used for the preparation of activated N-hydroxysuccinimide esters.

SUMMARY OF THE INVENTION

The present invention is a novel process for the production of amides in high yields and practically free of racemization. The process in accordance with the invention comprises reacting a carboxylic acid with a primary or secondary amine in the presence of a carbodiimide dehydrating agent and a catalytic amount of an N-hydroxy compound.

It has been found that when only catalytic amounts of an N-hydroxy compound is used in the reaction of a carboxylic acid with a primary or secondary amine and a carbodiimide dehydrating agent, amides can be produced with considerable reduction in reaction byproducts. Furthermore, such reaction yields amides in high yields and practically without racemization.

DETAILED DESCRIPTION OF THE INVENTION

The present invention is a novel process for the production of amides, including peptides, by reacting a carboxylic acid with a primary or secondary amine in the presence of a carbodiimide dehydrating agent and a catalytic amount of an N-hydroxy compound.

As used throughout this specification, "alkyl"—alone or in combination—refers to any straight or branched-chain alkyl group having from 1 to 15 carbon atoms. "Lower alkyl" refers to those straight or branched-chain alkyl groups having from 1 to 7 carbon atoms. As used throughout this specification, "heteroaryl" or "heteroaromatic" refers to any aryl or aromatic ring structure containing at least one heteroatom in this ring structure, which heteroatom is selected from the group consisting of nitrogen, sulfur and oxygen. As used through this specification, "peptide" refers to any amide formed from two or more amino acids, such that a —NCO— functional group is formed by the interaction between an amino group of one amino acid and a carboxyl group of another amino acid. As used herein, the term "peptide" includes polypeptides.

This invention provides for the production of amides, including peptides, by the interaction of any carboxylic acid and any primary or secondary amine in the presence of an organic N-hydroxy compound and a carbodiimide dehydrating agent. The novelty of this invention resides in the fact that only catalytic amounts of an organic N-hydroxy compound are needed to facilitate the interaction between the carboxylic acid and the primary or secondary amine, and that in using catalytic amounts of such N-hydroxy compound, amides are produced in high yield practically free of racemization.

The "carboxylic acids" used in accordance with this invention may be any carboxylic acid and include aliphatic, aromatic, aromatic-aliphatic, heteroaromatic, heteroaromatic-aliphatic carboxylic acids, which carboxylic acids may be substituted or unsubstituted. Other "carboxylic acids" which can be utilized include natural N-acylated α-amino acids having the L configuration, homologues of such natural amino acids, and epimers of such amino acids with the D-configuration, which amino acids, homologues and epimers thereof may be substituted or unsubstituted.

A "homologue" of a natural N-acylated α-amino acid refers to such amino acids wherein the side-chain of the amino acid is lengthened or shortened by one or two methylene groups, or in which a methyl group of the side chain is replaced by hydrogen.

Any natural N-acylated α-amino acid, or homologue or epimer thereof, may be used as the carboxylic acid to react with amines to produce amides.

Examples of suitable amino acids or homologues or epimers thereof, include glycine, alanine, valine, norvaline, leucine, isoleucine, norleucine, serine, homoserine, threonine, methionine, cysteine, proline, trans-3-hydroxyproline, trans-4-hydroxyproline, phenylalanine, 4-aminophenylalanine, 4-chlorophenylalanine, 4-nitrophenylalanine, tyrosine, tryptophan, cyclohexylalanine, cyclohexylglycine, indoline-2-carboxylic acid, 1,2,3,4-tetrahydroisoquinoline-3-carboxylic acid, aspartic acid, asparagine, histidine, arginine, lysine, α,β-diaminopropionic acid, α,γ-diaminobutyric acid, ornithine, δ-hydroxylysine, glutamic acid mono-t-butyl ester, glutamine, N-dimethylglutamine, glutamic acid, aminomalonic acid, aminomalonic acid monoamide, N-pivaloylornithine, and N-t-butoxycarbonyllysine.

The N-acylated α-amino acids also include any N-acylated α-amino acid, or homologue or epimer thereof, wherein the carboxy group in the amino acid side-chain is esterified, e.g. as an alkyl ester, or amidated as a carbamoyl, alkylcarbamoyl, or dialkylcarbamoyl. Examples of such alkyl esters are methoxycarbonyl and t-butoxycarbonyl. When t-butoxycarbonyl is the alkyl moiety in the alkyl ester, N-acylated glutamic acid mono-t-butyl ester is an example of such carboxylic acid. Acylated aminomalonic acid monoamide is an example of a carbamoylated, N-acylated α-amino acid. The preferred alkylcarbamoyl and dialkylcarbamoyl groups are methylcarbamoyl and dimethylcarbamoyl, respectively.

Suitable N-acyl amino groups in the N-acylated α-amino acids or homologues or epimers thereof include alkanoylamino, alkoxycarbonylamino, or arylalkoxycarbonylamino. When alkanoylamino, acetylamino or pivaloylamino are enumerated. When alkoxycarbonylamino, t-butoxycarbonylamino is preferred. The preferred arylalkoxycarbonylamino is benzyloxycarbonylamino.

In addition, any N-acylated α-amino acid, or homologue or epimer thereof, wherein the hydroxy group in the side chain is present in etherified or esterified form, as an alkoxy group such as methoxy, as an arylalkoxy group, such as benzyloxy, or as a lower alkanoyloxy group, such as acetoxy, may also be used as a carboxylic acid in accordance with this invention.

The amino acid side-chain of the above-mentioned N-acylated α-amino acids, or homologues or epimers thereof, may be any amino acid side-chain. Thus, the amino acid side chain can be arylalkyl, heteroarylalkyl, hydrogenated arylalkyl, hydrogenated heteroarylalkyl or alkyl, all of them may be substituted or unsubstituted.

When the side-chain is arylalkyl, the aryl residue may be unsubstituted or substituted.

As an example of an unsubstituted aryl, phenyl is enumerated, and the corresponding preferred amino acids are phenylglycine, phenylalanine and phenylserine. The aryl residue may be substituted with one or more of the following groups: alkyl, halogen, hydroxy, alkoxy, alkanoyloxy, amino, alkylamino, dialkylamino, alkanoylamino, alkoxycarbonylamino, arylmethoxycarbonylamino and/or nitro.

When the substitution group is alkyl, methyl is preferred. When the substitution group is halogen, any halogen may be used, such as fluorine, chlorine, bromine or iodine, and the corresponding amino acid is e.g. 4-cholorophenylalanine. Methoxy is the preferred alkoxy group, and acetoxy is the preferred alkanoyloxy group. When the substitution group is alkylamino, methylamino may be enumerated. When amino is the substitution group, 4-aminophenylalanine is the preferred amino acid. When the substitution group is dialkylamino, dimethylamino is enumerated. The preferred alkanoylamino groups are acetylamino and pivaloylamino. The preferred alkoxycarbonylamino group is t-butoxycarbonylamino. When the substitution group is arylmethoxycarbonylamino, benzyloxy-carbonylamino and 9-fluorenylmethoxycarbonylamino are enumerated. 4-Nitrophenylalanine is the preferred amino acid when nitro is the substitution group.

N-acylated α-amino acids also include N-acylated benz-fused phenylalanine or phenylglycine, such as α-naphthylalanine, or a 5- or 6-membered cyclic benz-fused N-acylated α-amino acid, e.g. indoline-2-carboxylic acid or 1,2,3,4-tetrahydroisoquinoline-3-carboxylic acid.

When the amino acid side-chain is a hydrogenated arylalkyl, cyclohexylalkyl is the preferred group, such as in cyclohexylalanine or cyclohexylglycine.

The N-acyl groups of the N-acyl α-amino acids, or homologues or epimers thereof, may be alkanoyl, alkoxycarbonyl, arylalkoxycarbonyl, an acyl residue of an aromatic-aliphatic or heteroaromatic carboxylic acid referred to above, an amino acid referred to above, including homologues or epimers thereof; or a dipeptide consisting of two of the aforementioned amino acids, including homologues and epimers thereof.

The carboxylic acids used in this invention to react with an amine to produce amides may be aliphatic, which aliphatic group may be substituted or unsubstituted. Examples of unsubstituted aliphatic acids are propionic acid and isobutyric acid. Examples of a suitable substituted aliphatic carboxylic acid include 2-phthalimidoisobutyric acid, (R)-lactic acid and (S)-lactic acid.

When the N-acyl group is alkanoyl, acetyl or pivaloyl, e.g. N-pivaloyl-ornithine, is preferred. When alkoxycarbonyl, t-butoxycarbonyl may be enumerated. The preferred arylmethoxy-carbonyl is benzyloxy-carbonyl, and N-(benzyloxycarbonyl)-L-asparagine and N-(benzyloxycarbonyl)-L-tyrosine are examples of corresponding N-acylated amino acids. As examples of acyl residues of aromaticaliphatic carboxylic acids, (S)-α-[(t-butylsulphonyl)-1-methyl]-β-phenylpropionyl and (S)-α-[[[1-(morpholinocarbonyl)-1-methylethyl]sulphonyl]methyl]-β-phenylpropionyl are enumerated. An example of an acyl residue of a heteroaromatic carboxylic acid includes 2-quinolylcarbonyl. When the acyl residue is 2-quinolylcarbonyl, then N-(2-quinolylcarbonyl)-L-asparagine is the preferred N-acylated α-amino acid.

The carboxylic acid may also be substituted or unsubstituted aromatic. A suitable unsubstituted aromatic carboxylic acid is benzoic acid. Examples of a suitable substituted aromatic carboxylic acid includes 2-phthalimidoxyisobutyric acid, 3,4-dihydroxybenzoic acid, salicylic acid, 1-naphthoic acid, and 2-naphthoic acid.

The carboxylic acid used in accordance with this invention may also be aromatic-aliphatic, which aromatic-aliphatic group may be substituted or unsubstituted. The preferred unsubstituted aromaticaliphatic carboxylic acid is phenylacetic acid. The preferred substituted aromatic-aliphatic carboxylic acid includes p-hydroxyphenylacetic acid, (S)-α-[(t-butylsulphonyl)-methyl]hydrocinnamic acid, (S)-α-[[[1-(morpholinocarbonyl)-1-methylethyl]sulphonyl]methyl]hydrocinnamic acid.

Among the carboxylic acids used to react with an amine to produce amides include heteroaromatic carboxylic acids, such as 2-pyridinecarboxylic acid, 3-pyridine carboxylic acid, 4-pyridinecarboxylic acid, 2-pyrimidinecarboxylic acid, 4-pyrimidinecarboxylic acid, 5-chloro-2-pyridine carboxylic acid, 2-quinoline carboxylic acid, 3-quinoline carboxylic acid and isoquinoline-1-carboxylic acid.

When the carboxylic acid is heteroaromatic-aliphatic, (S)-1 -(t-butyoxycarbonyl)-α-[(S)-α-[(t-butyl-sulphonyl)methyl]hydrocinnamamido]imidazole-4-propionic acid, and (S)-(t-butoxycarbonyl)-α-[[[1-(morpholinocarbonyl)-1-methyl-ethyl]sulphonyl]methyl]hydrocinnamamido]imidazole-4-propionic acid, 2-pyridylacetic acid, 3-indolylacetic acid, 3-(3-indolyl)propionic acid, and (4-imidazolyl)acetic acid are preferred.

Any of the carboxylic acids enumerated above can be reacted with any primary or secondary amine in the presence of an N-hydroxy compound and a carbodiimide dehydrating agent to produce amides, in accordance with this invention. Any primary or secondary amine may be used in this invention.

The primary or secondary amine to be reacted with a carboxylic acid to produce an amide may include any amino acid enumerated above, including any homologue or epimer thereof, wherein there is at least one non-acylated amino group, and the acid group is protected. Any means of protecting the acid group may be used, such as by esterification.

Among the primary or secondary amines to be used in this invention include methyl esters of the amino acids enumerated above, such as histidine methyl ester, as well as t-butyl (2-aminoethyl)-carbamate, (1S,2R,3S)-3-amino-2(R)-hydroxy-4-phenylbutyl)-N-t-butyl-decahydro-(4aS,8aS)-isoquinoline-3(S)-carboxamide, (1S,2R,3S)-3-amino-4-cyclohexyl-1-cyclopropylbutene-1,2 diol and 2(3(S)-amine-2(R)-hydroxy-4-phenylbutyl)-N-t-butyl-decahydro-(4aS,8aS)-isoquinoline-3(S)-carboxamide, and t-butyl(4-piperidinyloxy)acetate.

In addition, primary or secondary amines to be utilized in the production of amides include alkylamines, dialkylamines, aralkylamines or $C_{3-6}$-alkylene-disubstituted amines, or hydrazine, which hydrazine may be substituted or unsubstituted. The hydrazine may be substituted with alkyl, such as methylhydrazine, or acyl, such as 3,4-dihydroxybenzoic acid hydrazide.

Any primary or secondary amine which can be used to react with a carboxylic acid to produce amides may contain any other groups which are inert under the reaction conditions. These primary or secondary amines may be optionally interrupted by an oxygen, sulphur, or a substituted nitrogen atom. The nitrogen atom may be substituted with an alkyl, phenylalkyl, alkanoyl or alkanoyloxy.

As set forth above, any carboxylic acid can be reacted with any amine in the presence of a carbodiimide dehydrating agent and an organic N-hydroxy compound to produce amides. Carbodiimides are known in the art to function as dehydrating agents in organic reactions. Any conventional carbodiimide dehydrating agent may be used.

Examples of preferable carbodiimides dehydrating agents are dicyclohexylcarbodiimide (DCC), diisopropylcarbodiimide (DIC), N-ethyl-N'-(3-dimethylaminopropyl)carbodiimide hydrochloride (EDC), N-cyclohexyI-N'-(β-[N-methylmorpholino]ethyl)carbodiimide p-toluenesulphonate and the like.

In carrying out this reaction of a carboxylic acid with an amine to produce an amide, the amount of carbodiimide dehydrating agent is not critical as long as said carbodiimide dehydrating agent is present in sufficient amounts to facilitate such reaction by dehydration to yield an amide. It is generally preferred when said carbodiimide dehydrating agent is present in molar amounts equivalent to the molar amount of carboxylic acid present in the reaction mixture.

The novelty of this invention directed to a process for producing amides from the reaction of a carboxylic acid with primary or secondary amines, in the presence of a carbodiimide dehydrating agent and an N-hydroxy compound, resides in the fact that the reaction proceeds in the presence of only catalytic amounts of an N-hydroxy compound to produce amides in high yield practically free of racemization.

An N-hydroxy compound is any conventional organic compound having a >N—C)H— functional group. Any conventional N-hydroxy compound may be used in this invention, such as N-hydroxysuccinimide, 1-hydroxybenzotriazole, 3-hydroxy-4-oxo-3,4-dihydro-1,2,3-benzotriazine, 1-hydroxy-2-oxoindoline, 3-hydroxy-4-oxo-3,4-dihydroquinazoline, 1-hydroxy-2(1H)-pyridone and the like.

The organic N-hydroxy compound must be present in sufficient amounts to catalyze the reaction. Preferably, the N-hydroxy compound is present in a molar equivalent amount of not less than 1% and not more than 60% of the molar equivalent of carboxylic acid present in the reaction mixture. Best results are obtained when the N-hydroxy compound is present in the amount of 3–25% of the molar amount of carboxylic acid.

The reaction of a carboxylic acid with a primary or secondary amine is carried out in a manner known per se, conveniently in an organic solvent or solvent mixture which is inert under the reaction conditions. Any conventional organic solvent may be used. Among the preferred solvents include such as ethyl acetate, acetone, acetonitrile, dimethylformamide, methylene chloride, tetrahydrofuran and the like.

The temperature is not critical; however a temperature between about 0° C. and 50° C. is preferred. Best results are obtained when the temperature is room temperature.

Solid phase synthesis methods can also be used to react a carboxylic acid with an amine to produce amides in accordance with this invention, when the primary of secondary amine contains a carboxyl group. Any solid phase synthesis method may be used. These solid phase synthesis methods are especially suitable for the manufacture of peptides, in which case the amide coupling is carried out several times in succession. When solid phase synthesis methods are used, it is preferable to use as the N-acylated α-amino acids described above, which are protected at the amino group by t-butoxycarbonyl or 9-fluorenylmethoxycarbonyl. Suitable carriers are polystyrene or polyamide resins, such as p-benzyloxy-benzyl alcohol-polystyrene resin, p-hydroxymethylphenoxy-polystyrene resin, 4-(2',4'-dimethoxyphenyl-hydroxymethyl)-phenoxy-polystyrene resin, dimethylacrylamide-polyamide resin, glycylacrylamide-polyamide resin, siliceous earth/polyamide resin and the like. The desired peptide can be cleaved off readily from the carrier resin, for example using trifluoroacetic acid and the like.

In the following Examples, which illustrate the present invention but which are not intended to limit its scope in any manner, all temperatures are given in degrees Celsius.

EXAMPLE 1

17.9 g (74 mmol) of histidine methyl ester dihydrochloride, is 70 ml of acetonitrile and 20.6 ml (148 mmol) of triethylamine were stirred at 20° for 2 hours. 20 g (70 mmol) of (S)-α-[(t-butylsulphonyl)methyl]hydrocinnamic acid, 0.78 g (7 mmol) of 1-hydroxy-2(1H)-pyridone and 140 ml of ethyl acetate were subsequently added. After 15 minutes a solution of 15.2 g (74 mmol) of dicyclohexylcarbodiimide in 90 ml of ethyl acetate was added within 30 minutes. The reaction had finished after stirring at 20° for 18 hours. The solid (dicyclohexylurea) was filtered off under suction and the filtrate was washed with aqueous sodium bicarbonate solution and water. 32.3 g of methyl (S)-α[(t-butylsulphonyl)methyl]hydrocinnamamido]imidazolepropionate were obtained as a white foam (HPLC content 94%; content-corrected yield: 98%).

EXAMPLE 2

2.5 g (10.5 mmol) of histidine methyl ester dihydrochloride, 10 ml of acetonitrile and 2.9 ml (148 mmol) of triethylamine were stirred at 20° for 20 hours. 3.8 g (10 mmol) of (S)-α[[[1-(morpholinocarbonyl)-1-methylethyl] sulphonyl]methyl]hydrocinnamic acid, 0.11 g (1 mmol) of 1-hydroxy-2(1H)-pyridone and 20 ml of ethyl acetate were subsequently added. After 15 minutes a solution of 2.2 g (10.5 mmol) of dicyclohexylcarbodiimide in 15 ml of ethyl acetate was added within 30 minutes. The reaction had finished after stirring at 20° for 18 hours. The solid (dicyclohexylurea) was filtered off under suction and the filtrate was washed with aqueous sodium bicarbonate solution and water. 5.4 g of N-[(S)-α-[[[1-methyl-1-(morpholinocarbonyl)ethyl]sulphonyl]methyl]hydrocinnamoyl]-L-histidine methyl ester were obtained.

EXAMPLE 3

89 g (170 mmol) of (S)-1-(t-butoxycarbonyl)-α-[(S)-α-[(t-butylsulphonyl)methyl]hydrocinnamamido]imidazole-4-propionic acid, 1 g (8.5 mmol) of N-hydroxysuccinimide, 35.5 g (155 mmol) of (1S,2R,3S)-3-amino-4-cyclohexyl-1-cyclopropyl-butane-1,2-diol and 800 ml of ethyl acetate were stirred at 20°. A solution of 37 g (178 mmol) of dicyclohexylcarbodiimide in 110 ml of ethyl acetate was added within 10 minutes. The reaction had finished after stirring at 20° for 17 hours. The solid (dicyclohexylurea) was filtered off and the filtrate was treated while stirring firstly with 68 ml of deionized water and then with 1100 ml of hexane. After one hour at 0° the crystallizate was filtered off under suction and triturated in methanol at 20°. The suspension was cooled to −15° and the product was filtered off. 98.8 g (86%) of t-butyl 4-[(S)-2-[(S)-2-t-butanesulphonylmethyl-3-phenylpropionylamino]-2 -[(1S,2R,3S)-1-cyclohexylmethyl-3-cyclopropyl-2,3-dihydroxy-propylcarbamoyl]ethyl]-1H-imidazole-1-carboxylate were obtained.

EXAMPLE 4

11.7 g (44 mmol) of N-(benzyloxycarbonyl)-L-asparagine, 16.0 g (40 mmol) of 2-[3(S)-amino-2(R)-hydroxy-4-phenylbutyl]-N-t-butyl-decahydro-(4aS,8aS)-isoquinoline-3(S)-carboxamide and 0.46 g (4 mmol) of N-hydroxysuccinimide were suspended in 160 ml of tetrahydrofuran and 80 ml of ethyl acetate at 20°. A solution of 9.1 g (44 mmol) of dicyclohexylcarbodiimide and 80 ml of ethyl acetate was added dropwise within 15 minutes and the reaction mixture was stirred at 20°. The reaction had finished after 18 hours. The solid (dicyclohexylurea) was filtered off under suction. The filtrate was freed from tetrahydrofuran and the product was crystallized from ethyl acetate/hexane. The yield of cis-2-[3(S)-[[N-(benzyloxycarbonyl)-L-asparaginyl]amino]-2(R)-hydroxy-4-phenylbutyl]-N-t-butyl-decahydro-(4aS,8aS)-isoquinoline3(S)-carboxamide was 23.0 g (88%).

EXAMPLE 5

10.2 g (30 mmol) of N-(benzyloxycarbonyl)-L-tyrosine dihydrate, 6.48 g (30 mmol) of t-butyl (4-piperidinyloxy)acetate and 0.17 g (1.5 mmol) of N-hydroxysuccinimide were dissolved in 200 ml of ethyl acetate while stirring under argon. 6.5 g (31.5 mmol) of dicyclohexylcarbodiimide dissolved in 33 ml of ethyl acetate were added dropwise to the yellowish solution within 19 minutes. A suspension formed slowly and this was stirred at 22° for 22 hours. The precipitated dicyclohexylurea was filtered off and the filtrate was extracted with 1N hydrochloric acid, water and sodium chloride solution. The organic phase was dried over sodium sulphate and, after removing the drying agent, evaporated. 13.1 g of t-butyl [[1-[N-[(benzyloxy)carbonyl]-L-tyrosyl]-4-piperidinyl]oxy]acetate were obtained as a white, hard foam, the microanalysis of which corresponded to that of authentic material.

EXAMPLE 6

11.14 g (30 mmol) of N-(benzyloxycarbonyl)-O-(1,1-dimethylethyl)-L-tyrosine were dissolved in 65 ml of ethyl acetate while warming to 40°. The solution was treated at 20° with 0.1 g (0.9 mmol) of N-hydroxysuccinimide. Subsequently, a solution of 7.5 g (36 mmol) of dicyclohexylcarbodiimide in 40 ml of ethyl acetate was added dropwise at 22° within 25 minutes. A white suspension formed during the addition and this was stirred for 30 minutes. A solution of 7.8 g (36 mmol) of t-butyl (4-piperidinyloxy)acetate in 100 ml of ethyl acetate was then added dropwise to the suspension within 30 minutes. A suspension formed and this was stirred at 22° for 3 hours. The precipitated dicyclohexylurea was filtered off and the filtrate was washed with 2N hydrochloric acid, water and semi-saturated sodium bicarbonate solution. The organic phase was dried over sodium sulphate and, after removing the drying agent, evaporated. The residue was a viscous oil and weighed 18.5 g. The oil was diluted with a mixture of 10 ml of ethyl acetate and 60 ml of hexane and warmed to 50°. The insoluble solid was filtered off under suction and the filtrate was treated with 20 ml of hexane and seeded with a small amount of crystalline product at 30°. The mixture was cooled to 0° within one hour and stirred at this temperature for 30 minutes. The crystals were then filtered off under suction and washed on the filter with 20 ml of hexane. 14.5 g (85%) of benzyl [(S)-p-t-butoxy-α-[[4-[(t-butoxycarbonyl)methoxy]-piperidino]carbonyl]phenethyl]carbamate were obtained in this manner. Its content was 96% according to HPLC.

EXAMPLE 7

125.9 g (312 mmol) of 2-(3(S)-amino-2(R)-hydroxy-4-phenylbutyl)-N-t-butyl-decahydro-(4aS,8aS)-isoquinoline-3(S)-carboxamide, 94.6 g (328 mmol) of N-(2-quinolylcarbonyl)-L-asparagine and 3.5 g (31 mmol) of 1-hydroxy-2(1H)-pyridone were treated with a mixture of 75 ml of tetrahydrofuran and 1925 ml of ethyl acetate. A solution of 70.9 g (344 mmol) of dicyclohexylcarbodiimide in 500 ml of ethyl acetate was subsequently added dropwise at 25° within 30 minutes while stirring. The reaction mixture was stirred for 10 hours. Then, 50 ml of water of low ion contents were added and the suspension was cooled to 2°–3° and stirred at this temperature for 1 hour. The dicyclohexylurea was then filtered off and washed on the filter with 2 500 ml portions of ethyl acetate. The filtrates were combined and treated slowly at 50° with a solution of 32.5 g (338 mmol) of methanesulphonic acid and 250 ml of ethyl acetate. The suspension was subsequently stirred at 20° for 14 hours. The crystals were then filtered off under suction, washed with a total of 600 ml of ethyl acetate and subsequently dried at 45°/2000 Pa for 24 hours. 229.5 g (95%) of N-t-butyl-decahydro-2-[2(R)-hydroxy-4-phenyl-3(S)-[[N-(2-quinolylcarbonyl)-L-asparaginyl]amino]butyl]-(4aS,8aS)-isoquinoline- 3(S)-carboxamide methanesulphonate having a HPLC content of 97.1% were obtained.

EXAMPLE 8

H-Val-Gln-Ala-Ala-Ile-Asp-Tyr-Ile-Asn-Gly-OH [SEQ ID NO:1] was prepared by solid phase synthesis using base-labile N-fluorenylmethoxycarbonyl-amino acids (Fmoc-amino acids), t-butyl side-chain protecting functions and p-benzyloxybenzyl alcohol-polystyrene resin as described by Atherton and Sheppard in "The Peptides; Analysis, Synthesis, Biology", vol. 9 (S. Udenfriend and J. Meienhofer, Eds.; Academic Press, New York [1987]). The synthesis was started using 4 g of Fmoc-Gly-OCH$_2$C$_6$H$_4$O—CH$_2$C$_6$H$_4$-resin having a loading of 0.5 mmol of Fmoc-Gly per gram of resin, i.e. using 2 mmol of substrate. A semi-automatic "Peptide Synthesizer" SP 640 from Labortec AG, CH-4416 Bubendorf was used. The following groups were used as side-chain protecting functions: The t-butyl ether for tyrosine and the t-butyl ester for aspartic acid. 2.5 mol equivalents of the subsequent Fmoc-amino acids based on the amino components coupled to the resin were used for each coupling step. 1 mol equivalent of DCC in the presence of 0.1 mol equivalent of 1-hydroxy-2(1H)-pyridone, based on the Fmoc-amino acid, was used as the coupling reagent. In difficult coupling steps, such as the coupling of valine to glutamine, a 1:1 solvent mixture of dimethylformamide (DMF) and 1,3-dimethyl-2-imidazolidinone was used.

| Programme for one cycle: | | |
|---|---|---|
| Operation | Solvent/Reagent | Repetitions/ Duration |
| Washing | DW | 2 × 1 min. |
| Deprotection | 20% piperidine in DMF | 1 × 3 min. |
| Deprotection | 20% piperidine in DMF | 1 × 10 min. |
| Washing | DMF | 4 × 0.5 min. |
| washing | Isopropanol | 2 × 0.5 min. |
| Stop | Ninhydrin test (must be positive) | |
| Washing | DMF | 2 × 1 min. |
| Stop | Addition of the next Fmoc-amino acid and of 0.1 mol equivalent of 1-hydroxy-2(1H)-pyridone in DMF | |
| Equilibration | | 1 min. |
| Stop | Addition of DCC | |
| Coupling | | 30 min. |
| Washing | DMF | 1 × 1 min. |
| Washing | Isopropanol | 2 × 1 min. |
| Stop | Ninhydrin test after coupling (must be negative) | |

After completion of the synthesis 0.5 g of decapeptide resin was shaken with trifluoroacetic acid/water (4:1) for 2 hours. The resin was filtered off and the filtrate was concentrated, the residue was digested with ether and the product (insoluble in ether) was lyophilized from water. The product weighed 125 mg and had the expected mol mass of 1063 in the mass spectrum (FAB).

EXAMPLE 9

16 g (0.1 mol) of t-butyl (2-aminoethyl)carbamate, 17.3 g (0.11 mol) of 5-chloro-2-pyridinecarboxylic acid and 1.1 g (0.01 mol) of 1-hydroxy-2(1H)-pyridone are stirred in 170 ml of acetonitrile at 20°. A solution of 22.7 g (0.11 mol) of dicyclohexylcarbodiimide in 200 ml of acetonitrile is added dropwise to the reaction mixture within 30 minutes. The reaction mixture is stirred at 20° overnight. Subsequently, the solid is filtered off under suction and the filtrate is evaporated in a water-jet vacuum. The residue is dissolved in 90 ml of methylene chloride and the solution is treated slowly with 120 ml of hexane, whereby t-butyl [2-(5-chloro-2-pyridinecarboxamido)ethyl]carbamate crystallizes out. The suspension is stirred at −10° for 90 minutes and the t-butyl [2-(5-chloro-2-pyridinecarboxamido)ethyl]carbamate is subsequently filtered off and dried at 35° in a vacuum drying oven.

EXAMPLE 10

16.9 g (0.11 mol) of 3,4-dihydroxybenzoic acid in 170 ml of tetrahydrofuran are treated with 5 g (0.1 mol) of hydrazine hydrate and 1.1 g (0.01 mol) of 1-hydroxy-2-(1H)-pyridone. A solution of 22.7 g (0.11 mol) of dicyclohexylcarbodiimide in 200 ml of tetrahydrofuran is added to the reaction mixture at 20° within 15 minutes. The reaction mixture is stirred at 20° for 16 hours. The resulting dicyclohexylurea is filtered off and the filtrate is evaporated. The residue is stirred with 60 ml of ethanol at 20° for 2 hours and the crystalline crude product is subsequently filtered off under suction and dried firstly in a water-jet vacuum and then in a high vacuum at 40°, whereby 3,4-dihydroxybenzoic acid hydrazide is obtained as a beige powder.

EXAMPLE 11

16.8 g (0.1 mol) of 3,4-dihydroxybenzoic acid hydrazide, 27.4 g (0.11 mol) of 2-phthalimidoxyisobutyric acid and 1.1 g (0.01 mol) of N-hydroxysuccinimide are suspended in 400 ml of tetrahydrofuran and the reaction mixture is treated at 25° within one hour with a solution of 13.9 g (0.11 mol) of diisopropylcarbodiimide in 200 ml of tetrahydrofuran. The reaction mixture is stirred at 25° for 24 hours. The solid is subsequently filtered off under suction and stirred intensively at 20° for 2 hours with 40 ml of isopropanol and 200 ml of t-butyl methyl ether. The crude product is filtered off under suction and dried for 15 hours in a water-jet vacuum at 40°, whereby 1-(3,4-dihydroxybenzoyl)-2-[2-methyl-2-(phthalimidoxy)propionyl]hydrazine is obtained.

---

---

We claim:

1. A process for the production of an amide comprising forming a reaction mixture of a carboxylic acid and (1S,2R, 3S)-3-amino-4-cyclohexyl-1-cyclopropyl-butane-1,2-diol;

and reacting said mixture in the presence of a carbodiimide dehydrating agent and a catalytic amount of an N-hydroxy compound selected from the group consisting of N-hydroxy-succinimide; 1-hydroxybenzotriazole; 3-hydroxy-4-oxo-3,4-dihydro-1-2-3-benzotriazine; 1-hydroxy-2-oxoindoline; 3-hydroxy-4-oxo-3,4-dihydroquinazoline; and 1-hydroxy-2(1H)-pyridone to form said amide.

2. A process for the production of an amide comprising forming a reaction mixture of a carboxylic acid and 2-[3(S)-amino-2(R)-hydroxy-4-phenylbutyl]-N-t-butyl-decahydro-(4aS,8aS)-isoquinoline-3(S)-carboxamide; and reacting said mixture in the presence of a carbodiimide dehydrating agent and a catalytic amount of an N-hydroxy compound selected from the group consisting of N-hydroxy-succinimide; 1-hydroxybenzotriazole; 3-hydroxy-4-oxo-3,4-dihydro-1-2-3-benzotriazine; 1-hydroxy-2-oxoindoline; 3-hydroxy-4-oxo-3,4-dihydroquinazoline; and 1-hydroxy-2(1H)-pyridone to form said amide.

3. The process of claim 2, wherein the carboxylic acid is N-(benzyloxycarbonyl)-L-asparagine.

4. The process of claim 2, wherein the carboxylic acid is N-(2-quinolylcarbonyl)-L-asparagine.

* * * * *